(12) United States Patent
Nagashima et al.

(10) Patent No.: US 6,818,243 B2
(45) Date of Patent: Nov. 16, 2004

(54) CRYSTALS OF ASPARTAME DERIVATIVE (75) Inventors: Kazutaka Nagashima, Kanagawa-ken (JP); Yuuichi Aoki, Kanagawa-ken (JP); Eriko Ono, Kanagawa-ken (JP); Tadashi Takemoto, Kanagawa-ken (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/183,652

(22) Filed: Jun. 28, 2002

(65) Prior Publication Data

US 2003/0009050 A1 Jan. 9, 2003

Related U.S. Application Data (63) Continuation of application No. PCT/JP00/09247, filed on Dec. 25, 2000.

(30) Foreign Application Priority Data

Dec. 28, 1999 (JP) ............................................. 11-373257

(51) Int. Cl.$^7$ ......................... A23L 1/236; C07C 229/00
(52) U.S. Cl. ......................................... 426/548; 560/40
(58) Field of Search ............................. 560/40; 426/548

(56) References Cited

U.S. PATENT DOCUMENTS 5,480,668 A * 1/1996 Nofre et al. ................. 426/548
6,548,096 B1 * 4/2003 Amino et al. ............... 426/548

FOREIGN PATENT DOCUMENTS

| EP | 0 533 222 | 3/1993 |
| JP | 9-249692 | 9/1997 |
| JP | 10-36389 | 2/1998 |
| WO | WO 99/52937 | 1/2001 |
| WO | WO 99/58554 | 2/2001 |

* cited by examiner

*Primary Examiner*—Johann Richter
*Assistant Examiner*—Paul A. Zucker
(74) *Attorney, Agent, or Firm*—Oblon, Spivak, McClelland, Maier & Neustadt, P.C.

(57) ABSTRACT

N-[N-[3-(3-hydroxy-4-methoxyphenyl)propyl]-L-α-aspartyl]-L-phenylalanine 1-methyl ester useful as a sweetener with a high potency of sweetness, is provided in the crystalline form having a high stability and a good purity which is favorable as a commercial product.

11 Claims, 4 Drawing Sheets

CRYSTALS OF ASPARTAME DERIVATIVE

CROSS-REFERENCE TO RELATED APPLICATIONS

This application is a continuation of International Application Serial No. PCT/JP00/09247, filed on Dec. 25, 2000, incorporated herein by reference, which claims priority to Japanese Patent Application Serial No. JP 11-373257, filed on Dec. 28, 1999, incorporated herein by reference.

BACKGROUND OF THE INVENTION

1. Field of the Invention

The present invention relates to N-[N-[3-(3-hydroxy-4-methoxyphenyl)propyl]-L-α-aspartyl]-L-phenylalanine 1-methyl ester in the crystalline form, which is useful as a sweetener.

2. Description of the Background

In recent years, as eating habits have been improved to a high level, obesity caused by excessive sugar intake and diseases accompanied by obesity have become important health problems. Accordingly, the development of a low-calorie sweetener (sweetening agent) that replaces sugar has been in great demand. As a sweetener that has been widely used at present, there is aspartame which is excellent in safety and quality of sweetness. And, some novel aspartame derivatives are excellent as sweeteners with respect to the degree (potency) of sweetness or the like as compared to aspartame have been found, see WO 99/52937.

Among such aspartame derivatives, N-[N-[3-(3-hydroxy-4-methoxyphenyl)propyl]-L-α-aspartyl]-L-phenylalanine 1-methyl ester, which is referred to as "object compound" or the like herein, is a particularly suitable sweetener. In this respect, in the above described international patent publication WO 99/52937, a process for purifying N-[N-[3-(3-hydroxy-4-methoxyphenyl)propyl]-L-α-aspartyl]-L-phenylalanine 1-methyl ester through the step of subjecting a concentrated reaction solution containing the compound to preparative thin layer chromatography (PTLC) is described. However, in the PTLC, the solid material obtained by concentrating the fraction extracted containing the object compound to solidification is in the amorphous form and is low in stability, and not high in purity. Therefore, it is not desirable for a commercial product. Accordingly, there remains a need an improved means of preparing this compound.

SUMMARY OF THE INVENTION

The problem to be solved by the present invention is to provide N-[N-[3-(3-hydroxy-4-methoxyphenyl)propyl]-L-α-aspartyl]-L-phenylalanine 1-methyl ester as a crystal which is high in stability and also good in purity, and therefore which is desirable for making the compound a commercial product.

The present inventors have earnestly studied this problem described, and, as a result, have found a crystal of N-[N-[3-(3-hydroxy-4-methoxyphenyl)propyl]-L-α-aspartyl]-L-phenylalanine 1-methyl ester, while the compound was heretofore only in the amorphous form, to reach to a completion of the present invention. The crystal thus found is excellent in stability and purity.

Thus, the present invention provides the following:

(1) A crystal of N-[N-[3-(3-hydroxy-4-methoxyphenyl)propyl]-L-α-aspartyl]-L-phenylalanine 1-methyl ester.

(2) A crystal of N-[N-[3-(3-hydroxy-4-methoxyphenyl)propyl]-L-α-aspartyl]-L-phenylalanine 1-methyl ester, which exhibits X-ray diffraction peaks at least diffraction angles of 8.2°, 14.7°, 20.5° and 22.4° (2θ, CuK α ray) when determined in the powder X-ray diffractometry, which hereinafter may be referred to as "A-type crystal".

(3) A crystal of N-[N-[3-(3-hydroxy-4-methoxyphenyl)propyl]-L-α-aspartyl]-L-phenylalanine 1-methyl ester, which exhibits X-ray diffraction peaks at least diffraction angles of 4.8°, 7.3°, 9.9° and 20.0° (2θ, CuK α ray) when determined in the powder X-ray diffractometry, which hereinafter may be referred to as "B-type crystal".

(4) A crystal of N-[N-[3-(3-hydroxy-4-methoxyphenyl)propyl]-L-α-aspartyl]-L-phenylalanine 1-methyl ester, which exhibits X-ray diffraction peaks at least diffraction angles of 4.7°, 8.0°, 9.0°, 14.0°, 20.2° and 24.3°(2θ, CuK α ray) when determined in the powder X-ray diffractometry, which hereinafter may be referred to as "C-type crystal".

In the present invention, N-[N-[3-(3-hydroxy-4-methoxyphenyl)propyl]-L-α-aspartyl]-L-phenylalanine 1-methyl ester, which is a sweetener with a high potency of sweetness, is be obtained in the crystalline form. Such a crystalline product is favorable as a commercial (industrial) product. In addition, the crystalline form of the compound has excellent stability and high purity.

Thus, the present invention also provides a method of sweetening a food or beverage product, comprising incorporating the crystal described above into a food or a beverage product.

The present invention also provides a food or beverage composition comprising a food or a beverage and the crystal described above.

A more complete appreciation of the invention and many of the attendant advantages thereof will be readily obtained as the same becomes better understood by reference to the following Figures in conjunction with the detailed description below.

DETAILED DESCRIPTION OF THE INVENTION

The chemical structure of N-[N-[3-(3-hydroxy-4-methoxyphenyl)propyl]-L-α-aspartyl]-L-phenylalanine 1-methyl ester of the present invention is represented by the following formula (1):

(1)

N-[N-[3-(3-hydroxy-4-methoxyphenyl)propyl]-L-α-aspartyl]-L-phenylalanine 1-methyl ester can be, for example, synthesized according to the process reported in the international patent publication WO 99/52937 described above, and incorporated herein by reference. Thus, it can be synthesized by the steps of reacting β-O-benzyl-α-L-aspartyl-L-phenylalanine methyl ester with 3-benzyloxy-4-methoxycinnamaldehyde to form N-[N-[3-(3-benzyloxy-4-methoxyphenyl)propenyl]-β-O-benzyl-L-α-aspartyl]-L-phenylalanine -1-methyl ester, and subjecting the resulting compound to a catalytic reduction with palladium on activated carbon (palladium carbon).

In addition, the compound can be synthesized by the following methods. Thus, the object compound of N-[N-[3-(3-hydroxy-4-methoxyphenyl)propyl]-L-α-aspartyl]-L-phenylalanine 1-methyl ester can be synthesized efficiently and in a high yield, by the step of subjecting 3-(3-hydroxy-4-methoxyphenyl)propionaldehyde and aspartame to a reductive alkylation reaction, for example, in a solvent such as alcohol and alcohol containing water, for example, in the presence of palladium-based catalyst or the like such as palladium on activated carbon, preferably under hydrogen pressure of 0.1–1.0 MPa or so, preferably at a reaction temperature of 15–50° C. or so (see the Examples described below).

3-(3-hydroxy-4-methoxyphenyl)propionaldehyde can be synthesized, for example, by the following methods.

First, the carbon-carbon double bond in 3-hydroxy-4-methoxycinnamic acid is reduced with palladium-based catalyst or the like such as palladium on activated carbon, preferably under hydrogen pressure of 0.1–1.0 MPa or so, preferably at a reaction temperature of 30–50° C. or so, to form 3-(3-hydroxy-4-methoxyphenyl)propionic acid. Subsequently, the compound is converted to an aldehyde through half reduction (semi-reduction, partial reduction; a reduction process for converting a carboxyl group into the corresponding formyl group) of the carboxylic acid by using a palladium-based compound such as pivalic acid anhydride and palladium acetate, and a triphenyl phosphine derivative such as triphenyl phosphine, based on the process disclosed in Chemistry Letters, 1998, vol. 11, 1143, incorporated herein by reference, whereby 3-(3-hydroxy-4-methoxyphenyl)propionaldehyde can be synthesized (see the Reference Examples described below).

A particular form of N-[N-[3-(3-hydroxy-4-methoxyphenyl)propyl]-L-α-aspartyl]-L-phenylalanine 1-methyl ester is not required to be subjected to a crystallization process, in order to obtain the desired crystal in the present invention. For example, the starting material for the crystallization may be the amorphous form, a reaction solution containing the object compound and the like. In addition, crude crystals which were once obtained after a crystallization process, and then the crystals can be subjected again to a crystallization process.

For example, in case that there is any insoluble material undesirable for the crystallization process in the solution, for example, the catalyst such as palladium carbon used, or the like, the material may be removed by separation through filtration or the like.

In case that the solution containing the object compound may possibly be one with a solvent suitable for the crystallization to obtain the crystals in the present invention, the solution as it is can also be used for the crystallization process. The solution is concentrated, for example, by concentration under reduced pressure or the like, up to a condition suitable for the crystallization of the object compound in the present invention, and thereafter, the solution thus concentrated can be used therefor. The solution containing the object compound is concentrated or the solvent thereof is distilled off completely, and thereafter a crystallization solvent suitable for obtaining the crystals of the present invention is added thereto secondarily up to a condition suitable for the crystallization, and thus obtained solution can be also used for the crystallization process.

Alternatively, in case that the solution containing the object compound uses a solvent undesirable for a crystallization of the object compound, after the solvent thereof is completely distilled off, for example, by concentration under reduced pressure, or the solution is concentrated to a solution to the effect that the solvent thereof does not affect on the crystallization, a suitable crystallization solvent can be added thereto, and thus obtained solution can also be used for the crystallization.

Alternatively, the crystallization process can be conducted by substitution of solvent to change the solvent in the solution to a suitable solvent for the crystallization thereof.

Usually, in the reaction solution containing the object compound described above, the raw materials for reaction such as aspartame and aldehyde, and by-product and the like are contained therein. The crystallization process in the present invention is also effective for removing these impurities from the object compound.

In this respect, in the case where a nonpolar impurity such as 3-(3-hydroxy-4-methoxyphenyl)propionaldehyde used as a reaction raw material is contained in the object compound to be subjected to the crystallization process, the object compound is first crystallized with an organic solvent, if required, to obtain once the crude crystals thereof, and thereafter thus obtained crude crystals are subjected further to a crystallization process, whereby the nonpolar impurity can also be efficiently removed.

Alternatively, to remove such nonpolar impurity, an extraction with a solvent can be also conducted in combination with the crystallization process. Such extraction with a solvent can also be conducted desirably in the state where the object compound is dissolved therein. However, it may be conducted in the state where the object compound is not completely dissolved therein, i.e., in the slurry state. For the other method, in the case where the synthetic reaction solution described above is subjected to a process for the extraction with a solvent, the reaction solution is concentrated or the solvent thereof is distilled off, where necessary, and thereafter thus obtained product may be used therefor.

In this respect, in the water layer in the extraction with a solvent, a solvent, which may be used as a reaction solvent for synthesizing the object compound, unless the solvent inbibits the separation nature of layer when extracting, may be used. The solvent includes methanol, ethanol, isopropyl alcohol, tetrahydrofuran, acetonitrile, acetic acid, and the like.

For a suitable solvent used for the extraction with a solvent in the present invention, an organic solvent which does not form a homogeneous solution with water when mixing, may be used. The organic solvent includes toluene, diethyl ether, methyl t-butyl ether, methyl acetate, ethyl acetate, propyl acetate, isopropyl acetate, butyl acetate and the like. The solvent can be also used in a form of mixed solvent containing more than one of these solvents.

A process for production of N-[N-[3-(3-hydroxy-4-methoxyphenyl)propyl]-L-α-aspartyl]-L-phenylalanine 1-methyl ester in the crystalline form having the A-type crystal as the crystal type involved in the present invention is described below.

In the crystallization process to obtain A-type crystal thereof, the crystallization process is conducted under the presence of sufficient amount of water, in the organic solvent. That is to say, the crystallization is conducted in a mixed solvent containing a good solvent which dissolves the object compound and water.

For the good solvent to dissolve the object compound, methanol, ethanol, isopropanol, acetone, tetrahydrofuran and acetonitrile which are polar solvents, can be cited. Particularly, methanol, ethanol and isopropanol which are alcohols, are desirable. For an amount of water needed for obtaining the A-type crystal, usually 6 molar equivalents or more, preferably 10 molar equivalents or more, and more preferably 15 molar equivalents or more of water, is used to the object compound. Water may also become a poor (bad) solvent for the object compound. In this respect, the other organic solvent which is a poor solvent thereto may be added thereto, if necessary. For such organic solvent, methyl acetate, ethyl acetate, propyl acetate, isopropyl acetate, butyl acetate, diethyl ether, methyl t-butyl ether and toluene are examples. In this respect, the crystallization may be conducted in the solvent which is in the form of separated layers (2 phase type).

For the crystallization process, which is not particularly limited, a crystallization with concentration, a crystallization with cooling, and the like can be used. Preferably, the crystallization may be conducted through the crystallization with cooling. In this respect, in the crystallization, the object compound is dissolved in the mixed solvent containing the good solvent and the poor solvent to prepare a homogeneous solution, and thereafter the solution may be subjected to cooling or the like for crystallization. In addition, a process through the steps of dissolving the object compound in a good solvent, and thereafter adding a poor solvent thereto for crystallization, or a process through the step of adding a good solvent in which the object compound has been dissolved, into a poor solvent for crystallization, or the like may be used.

In this respect, seed crystals therefor may be added to the crystallization solution during the crystallization process, if necessary. The seed crystals may be in the form of a slurry or the like. A process for aging the crystals may be incorporated in the crystallization process under way, if necessary.

The concentration of the object compound in the solution subjected to the crystallization process, may be usually 0.5–30 g/dl or so, preferably 1–15 g/dl or so, and more preferably 2–10 g/dl or so. If the concentration is too low, the yield for the crystallization may be lowered, and if the concentration is too high, a degree of purity for the crystals obtained may be lowered, and therefore they are not preferable.

The crystallizing temperature at the start of crystallization, may be usually 80° C. or lower, preferably 60° C. or lower, and more preferably 50° C. or lower. In case that the temperature is high too much, a problem, such as a decomposition of the object compound, a vaporization of the crystallization solvent, or the like may arise. The temperature for starting the nucleation is not particularly limited.

In case that a crystallization with cooling is conducted, for a temperature of cooling, the temperature at which the solution is not solidified may be selected. It may be cooled down to usually 20° C. or so, and preferably 10° C. or so. The speed for cooling is not particularly limited.

In addition, a continuous crystallization can be conducted, for example, at a temperature range of 80–10° C.

For a process for separation of crystals, there is no particular limitation thereto. Therefore, the usual and conventional means, such as separation with filtration and separation with centrifugation, can be used. For a process for drying the crystals after separation thereof, there is no particular limitations thereto. Therefore, usual and conventional means, such as a drying under reduced pressure and a drying under aerification (airthrough-flow drying). The drying under reduced pressure may be desirably used. The temperature for drying may be usually 60° C. to a room temperature (20° C.), and preferably 50–30° C. or so. The degree of humidity is not particularly limited.

The obtained A-type crystal involved in the present invention shows the following physical properties.

<Melting Point>

99° C. (Determination in the differential thermal analysis; Temperature range for the determination: 50–300° C.; heating-up speed: 10° C./minute.)

<Powder X-Ray Diffraction Pattern>

It exhibits characteristic peaks of diffractive X-ray in at least diffraction angles of 8.2°, 14.7°, 20.5° and 22.4° (2θ, CuK α ray) when determined in the powder X-ray diffractometry.

In this respect, it is presumed that the A-type crystal is in the mono hydrate form.

Next, a process for production of N-[N-[3-(3-hydroxy-4-methoxyphenyl)propyl]-L-α-aspartyl]-L-phenylalanine 1-methyl ester in the crystalline form having an B-type crystal as the crystal type, is described below.

For the crystallization solvent used in the crystallization process to obtain the B-type crystal, methanol, ethanol, isopropanol, acetone, tetrahydrofuran and acetonitrile, which are polar solvents, are examples of good solvents. Particularly, methanol, ethanol and isopropanol, which are alcohols, are desirable. For the poor solvents thereto, methyl acetate, ethyl acetate, propyl acetate, isopropyl acetate, butyl acetate, diethyl ether, methyl t-butyl ether and toluene, may be used.

In this case, in order to obtain the B-type crystal, it is desirable that water is not substantially contained in the crystallization solvent. In case that water is contained in the crystallization solvent, 1.5 molar equivalents at the most (1.5 molar equivalents or less), preferably 1.0 molar equivalents or less and further preferably 0.5 molar equivalents or less of the water may be used to the object compound.

The crystallization process is not particularly limited. The object compound is dissolved in the mixed solvent containing the good solvent and the poor solvent to prepare a homogeneous solution, and thereafter the solution as it is may be subjected to the crystallization process. In addition, a process through the steps of dissolving the object compound in a good solvent, and thereafter adding a poor solvent thereto for crystallization, or a process through the step of adding the good solvent in which the object compound has been dissolved, into a poor solvent for the crystallization, or the like may be used. In this respect, the crystallization may be conducted in the solvent which is in the form of separated layers (2 phase type). In this respect, seed crystals therefor may be added to the crystallization solution during the crystallization process, if necessary. The seed crystals may be in the form of a slurry or the like. A process for aging the crystals may be incorporated in the crystallization process under way of the crystallization, if necessary.

In addition, to obtain the B-type crystal, the temperature for starting the nucleation (point for nucleation) is adjusted to 15° C. or lower. In case that a cooling is conducted, for a temperature of cooling, the temperature at which the solution is not solidified may be selected. It may be cooled down to preferably 10° C. or so. The speed for cooling is not particularly limited. In addition, a continuous crystallization may be conducted at a temperature of 15° C. or lower.

A concentration of the object compound in the solution subjected to the crystallization process, may be usually 0.5–30 g/dl or so, preferably 1–15 g/dl or so, and more preferably 2–10 g/dl or so, in the same reason as above. As for a process for separation of crystals, there is no particular limitations thereto. Therefore, the usual and conventional means, such as separation with filtration and separation with centrifugation can be used.

As for a process for drying the crystals after separation thereof, there is no particular limitations thereto. Therefore, the usual and conventional means, such as a drying under reduced pressure and a drying under aerification (airthrough-flow drying). The drying under reduced pressure may be desirably used. The temperature for drying may be usually 60° C. to a room temperature (20° C.), and preferably 50–30° C. or so. In addition, the drying process may be conducted preferably under low humidity.

Thus obtained B-type crystal involved in the present invention shows the following physical properties.

<Melting Point>

123° C. (Determination in the differential thermal analysis; Temperature range for the determination: 50–300° C.; heating-up speed: 10° C./minute.)

<Powder X-Ray Diffraction Pattern>

It exhibits characteristic peaks of diffractive X-ray in at least diffraction angles of 4.8°, 7.3°, 9.9° and 20.0° (2θ, CuK α ray) when determined in the powder X-ray diffractometry.

In this respect, it is presumed that the B-type crystal is an anhydride.

A process for production of N-[N-[3-(3-hydroxy-4-methoxyphenyl)propyl]-L-α-aspartyl]-L-phenylalanine l-methyl ester in the crystalline form having an C-type crystal as the crystal type is described below.

For a crystallization solvent used in the crystallization process to obtain the C-type crystal, methanol, ethanol, isopropanol, acetone, tetrahydrofaran and acetonitrile, which are polar solvents, can be cited as good solvents thereto. Particularly, methanol, ethanol, and isopropanol, which are alcohols, are desirable. For a poor solvent thereto, methyl acetate, ethyl acetate, propyl acetate, isopropyl acetate, butyl acetate, diethyl ether, methyl t-butyl ether and toluene, may be used.

The crystallization process is not particularly limited. The object compound is dissolved in the mixed solvent containing the good solvent and the poor solvent to prepare a homogeneous solution, and thereafter the solution as it is may be subjected to the crystallization process. In addition, a process through the steps of dissolving the object compound in the good solvent, and thereafter adding the poor solvent thereto for crystallization, or a process through the step of adding the good solvent in which the object compound has been dissolved, into the poor solvent for crystallization, or the like may be used. In this respect, the crystallization may be conducted in the solvent which is in the form of separated layers (2 phase type). In this respect, seed crystals therefor may be added to the crystallization solution during the crystallization process, if necessary. The seed crystals may be in the form of a slurry or the like. A process for aging the crystals may be incorporated in the crystallization process under way, if necessary.

In order to obtain the crystals having the C-type crystal, an amount of water contained in the crystallization solvent is adjusted to usually 5 molar equivalents or less, and preferably 4 molar equivalents or less of the water to the object compound. In case that an amount of water contained in the crystallization solvent is in a range of approximately 1.5 molar equivalents to 5 molar equivalents or less of water to the object compound, a temperature for starting the nucleation (point for nucleation) is not particularly limited. It is conducted in a range of preferably at 10 to 80° C. or so, more preferably at room temperature (20° C.) to 60° C. or so, and further more preferably at room temperature (20° C.) to 50° C. or so. In case that an amount of water contained in the crystallization solvent is in a range of less than 1.5 molar equivalents, and particularly less than 1.0 molar equivalent of water to the object compound, it should be conducted at a temperature for starting the nucleation (point for nucleation) which may not become a low temperature. That is to say, it is conducted at a temperature for starting the nucleation (point for nucleation) of usually room temperature (20° C.) to 80° C. or so, preferably room temperature (20° C.) to 60° C. or so, and further more preferably room temperature (20° C.) to 50° C. or so. In addition, a continuous crystallization may be conducted at a temperature of 10 to 80° C. or so. A concentration of the object compound in the solution subjected to the crystallization process, may be 0.5–30 g/dl or so, preferably 1–15 g/dl or so, and more preferably 2–10 g/dl or so, in the same reason as above.

As for a process for separation of crystals, there is no particular limitations thereto. Therefor, usual and conventional means, such as separation with filtration and separation with centrifugation can be used. As for a process for drying the crystals after separation thereof, there is no particular limitations thereto. Therefor, usual and conventional means, such as a drying under reduced pressure and a drying under aerification (airthrough-flow drying). The drying under reduced pressure may be desirably used. The temperature for drying may be usually 60° C. to a room temperature (20° C.), and preferably 50–30° C. or so. A degree of humidity is not particularly limited.

The obtained C-type crystal involved in the present invention shows the following physical properties.

<Melting Point>

138° C. (Determination in the differential thermal analysis; Temperature range for the determination: 50–300° C.; heating-up speed: 10° C./minute.)

<Powder X-Ray Diffraction Pattern>

It exhibits characteristic peaks of diffractive X-ray in at least diffraction angles of 4.7°, 8.0°, 9.0°, 14.0°, 20.2° and 24.3° (2 θ, CuK α ray ) when determined in the powder X-ray diffractometry.

In this respect, it is presumed that the C-type crystal is an anhydride.

The A-type crystal, B-type crystal and C-type crystal provided in the present invention show an excellent stability, as also evident from the results of storage stability testing in the Example 11 described below.

Further, A-type crystal and C-type crystal become a further more excellent crystal in storage stability. In hygroscopic property (moisture absorption), A-type crystal and C-type crystal show an excellent characteristic property. In filtration property and separation property (dissolubility; isolation) of crystals, the A-type crystal is particularly excellent, and therefore becomes a particularly suitable crystal in the industrial production.

As described above, the present invention also provides a method of sweetening a food or beverage product, comprising incorporating the crystal described above into a food or a beverage product, and to the sweetened product obtained thereby. Suitable food and beverage products into which the crystal of the invention can be incorporated into are well-known to those skilled in the art such as, for example, products which are commonly sweetened with aspartame.

EXAMPLES

The present invention will be explained further in detail with reference to the following Reference Examples and Examples therefor. However, the present invention is not limited by the following Examples.

Reference Example 1

Production of 3-(3-hydroxy-4-methoxyphenyl) propionaldehyde 3-hydroxy-4-methoxycinnamic acid (15.0 g, 77.2 mmol) and 10% palladium on activated carbon having a water content of 50% (2.26 g) were added to a mixed solvent (330 ml) of methanol and water (Mixing Ratio of 10:1 v/v), and the mixture was stirred under a hydrogen atmosphere of ordinary pressure (0.1 MPa) at 50° C. for 5 hours for reaction. The obtained reaction solution was filtrated to remove the catalyst, and the filtrate obtained was concentrated under reduced pressure to solidification to obtain 3-(3-hydroxy-4-methoxyphenyl)propionic acid (15.1 g, 76.7 mmol, yield: 99%).

To a chemical reactor for hydrogenation under elevated pressure, 3-(3-hydroxy-4-methoxyphenyl)propionic acid (5.09 g, 25.9 mmol), pivalic acid anhydride (14.3 g, 76.6 mmol) and tetrahydrofuran (64 ml) were introduced, and thereafter the mixture was bubbled with nitrogen gas for 10 minutes. Palladium acetate (57 mg, 0.254 mmol) and triphenyl phosphine (349 mg, 1.33 mmol) were added thereto, and the mixture was bubbled with nitrogen gas for 20 minutes to substitute nitrogen gas completely for the gas in the system of reaction, whereby the system was filled with nitrogen gas. Next, hydrogen gas was added thereinto to substitute hydrogen gas for the gas in the system, and then the mixture was stirred under hydrogen pressure of 5.4 MPa at 80° C. for 24 hours for reaction. Thus obtained reaction solution was concentrated under reduced pressure to remove tetrahydrofuran by distillation. The remaining residue was purified with a silica gel column chromatography. The eluted fractions containing the object compound were concentrated under reduced pressure to obtain crude 3-(3-hydroxy-4-methoxyphenyl)propionaldehyde (2.26 g, 12.5 mmol, yield: 48%) in a slightly yellow colored solid form.

Thus obtained crude 3-(3-hydroxy-4-methoxyphenyl) propionaldehyde was recrystallized with toluene to obtain pure 3-(3-hydroxy-4-methoxyphenyl)propionaldehyde (1.94 g, 10.8 mmol, crystallization yield: 86%) in a white crystalline form.

Reference Example 2

Production of Amorphous N-[N-[3-(3-hydroxy-4-methoxyphenyl)propyl]-L-α-aspartyl]-L-phenylalanine 1-methyl Ester To N-t-butoxycarbonyl-β-O-benzyl-α-L-aspartyl-L-phenylalanine 1-methyl ester (12.2 g, 25.8 mmol), 4N-HCl/dioxane solution (129 ml) was added, and the mixture was stirred for 1 hour at room temperature. The reaction mixture was concentrated under reduced pressure, and to thus concentrated solution, 5% sodium hydrogen carbonate aqueous solution (750 ml) was added, and the mixture was extracted with ethyl acetate (750 ml) twice. The organic layer was washed with a sodium chloride-saturated aqueous solution, and dried with anhydrous magnesium sulfate. The magnesium sulfate was removed by filtration, and thus obtained filtrate was concentrated under reduced pressure to obtain β-O-benzyl-α-L-aspartyl-L-phenylalanine methyl ester (9.81 g, 25.5 mmol) as an oily matter.

β-O-benzyl-α-L-aspartyl-L-phenylalanine methyl ester (7.50 g, 19.5 mmol) obtained above was dissolved in tetrahydrofuran (THF; 180 ml), and the solution was kept at 0° C. 3-Benzyloxy-4-methoxycinnamaldehyde (4.80 g, 17.9 mmol), acetic acid (1.0 ml, 17.9 mmol) and NaB(OAc)$_3$H (5.13 g, 24.2 mmol) were added thereto, and the mixture was stirred at 0° C. for 1 hour, and further at room temperature overnight. To the reaction solution, sodium hydrogen carbonate saturated aqueous solution (70 ml) was added, and the solution was extracted with ethyl acetate (200 ml) twice. The organic layer was washed with sodium chloride saturated aqueous solution, and dried with anhydrous magnesium sulfate. The magnesium sulfate was removed by filtration, and thus obtained filtrate was concentrated under reduced pressure. The residue was purified with silica gel column chromatography and thus obtained fractions eluted containing the object compound were concentrated under reduced pressure to obtain N-[N-[3-(3-benzyloxy-4-methoxyphenyl)propenyl]-β-O-benzyl-L-α-aspartyl]-L-phenylalanine 1-methyl ester (4.90 g, 7.70 mmol) as an oily matter.

N-[N-[3-(3-benzyloxy-4-methoxyphenyl)propenyl]-β-O-benzyl-L-α-aspartyl]-L-phenylalanine 1-methyl ester (4.86 g, 7.63 mmol) obtained above was dissolved in methanol (160 ml), and 10% palladium on active carbon in the water content of 50% (2.32 g) was added thereto. The mixture was subjected to a reduction reaction under hydrogen at room temperature for 3 hours. The catalyst was removed by filtration, and the filtrate was concentrated under reduced pressure. The residue was purified with silica gel column chromatography and thus obtained fractions eluted containing the object compound were concentrated under reduced pressure to solidification to obtain N-[N-[3-(3-hydroxy-4-methoxyphenyl)propyl]-L-α-aspartyl]-L-phenylalanine 1-methyl ester (2.00 g, 4.36 mmol) as a solid matter. (The purity in HPLC was approximately 87%.)

Figure 4:
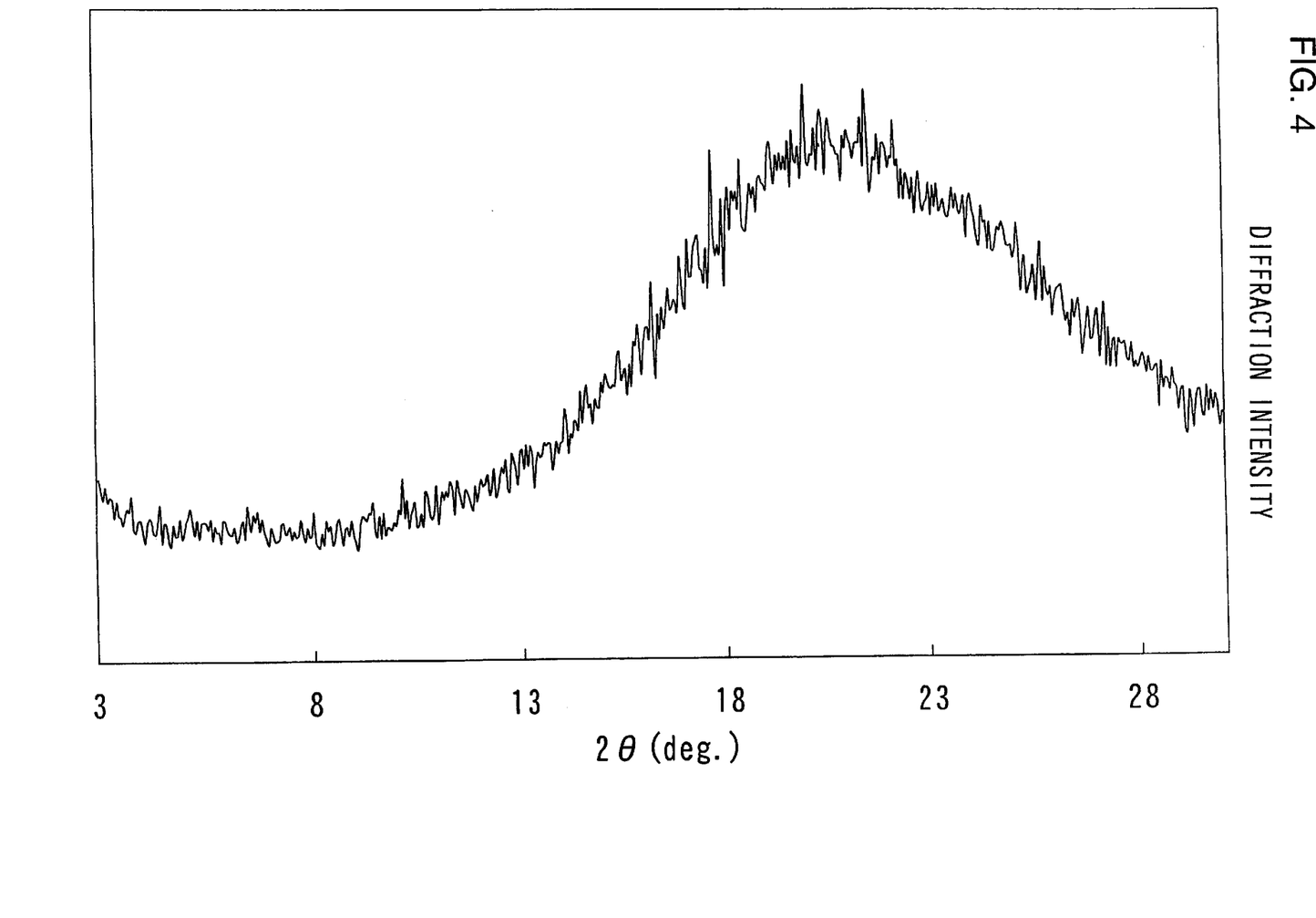
FIG. 4 is a powder X-ray diffraction pattern of amorphous form of N-[N-[3-(3-hydroxy-4-methoxyphenyl)propyl]-L-α-aspartyl]-L-phenylalanine 1-methyl ester.

For the solid matter obtained above, the diffractive X-ray was determined in the powder X-ray diffractometry by using CuK α ray. The obtained powder X-ray diffraction pattern therefor was shown in the FIG. 4. As is evident from the figure, the solid matter was in the amorphous form.

Example 1

Production of A-type Crystal of N-[N-[3-(3-hydroxy-4-methoxyphenyl) Propyl]-L-α-aspartyl]-L-phenylalanine 1-methyl Ester and Separation of the Crystal (1)

3-(3-hydroxy-4-methoxyphenyl)propionaldehyde (1.50 g, 8.32 mmol) and aspartame (2.57 g, 8.74 mmol) were added to a mixed solvent (86 ml) of methanol and water (Mixing ratio of 4:1 v/v), and 10% palladium on active carbon in the water content of 50% (0.77 g) was added thereto, and the mixture was stiffed under hydrogen atmosphere of ordinary pressure (0.1 MPa) at 35° C. for 48 hours for reaction. After completion of the reaction, the catalyst was removed by filtration, and the catalyst was further washed with methanol (20 ml). The filtrate and the wash solution were combined together to obtain a reaction solution (84.4 g, 100 ml) containing N-[N-[3-(3-hydroxy-4-methoxyphenyl)propyl]-L-α-aspartyl]-L-phenylalanine 1-methyl ester (2.69 g, 5.87 mmol). To the reaction solution, water (300 ml) and toluene (200 ml) were added, and the mixture was stirred at 40° C. for 30 minutes. The solution was made to separation of phases therein, and then toluene layer was removed to obtain a water layer (381 g). This aqueous layer was concentrated under reduced pressure at 50° C. to remove the solvent by distillation, and a mixed solvent (84 ml) of methanol and water (Mixing ratio of 1:3 v/v) were added thereto. The solid material was dissolved therein at 65° C., and thus obtained solution was cooled down to 10° C. (Cooling speed of 10° C./hour) to precipitate crystals. The mixture was stirred overnight at the same temperature, and thus obtained crystals were separated by filtration and washed with water (106 ml), and dried overnight under reduced pressure at room temperature to obtain N-[N-[3-(3-hydroxy-4-methoxyphenyl)propyl]-L-α-aspartyl]-L-phenylalanine 1-methyl ester (2.31 g, 5.05 mmol, crystallization yield: 86%, water content: 3.43 wt %). (The purity in HPLC was not less than 93%.)

For the crystals obtained above, diffractive X-ray was determined by using CuK α ray in the powder X-ray diffractometry. As a result, this crystal was in the crystalline form of A-type, which exhibits characteristic peaks of diffractive X-ray in at least diffraction angles of 8.2°, 14.7°, 20.5° and 22.4° (2 θ, CuK α ray) when determined in the powder X-ray diffractometry.

Example 2

Production of A-type Crystal of N-[N-[3-(3-hydroxy-4-methoxyphenyl)propyl]-L-α-aspartyl]-L-phenylalanine 1-methyl Ester and Separation of the Crystal (2)

3-(3-hydroxy-4-methoxyphenyl)propionaldehyde (33.7 g, 187 mmol) and aspartame (57.8 g, 196 mmol) were added to a mixed solvent (1926 ml) of methanol and water (Mixing ratio of 4:1 v/v), and 10% palladium on active carbon in the water content of 50% (17.3 g) was added thereto, and the mixture was stirred under hydrogen atmosphere of ordinary pressure (0.1 MPa) at 35° C. for 48 hours for reaction. After completion of the reaction, the catalyst was removed by filtration, and the catalyst was further washed with methanol (400 ml). The filtrate and the wash solution were combined together to obtain a reaction solution (1991 g, 2321 ml) containing N-[N-[3-(3-hydroxy-4-methoxyphenyl)propyl]-L-α-aspartyl]-L-phenylalanine 1-methyl ester (66.2 g, 144 mmol). This reaction solution was concentrated under reduced pressure at 50° C. to obtain a concentrated solution (183 g). To this concentrated solution, methanol (136 ml) and isopropyl acetate (2050 ml) were added, and the mixture was stirred at 65° C. for 40 minutes to dissolve the solid material, and then was cooled down to 10° C. (Cooling speed: 10° C./hour) to precipitate crystals. The mixture was stirred at the same temperature for 18 hours, and then the crystals were separated by filtration, and washed with isopropyl acetate (302 ml). The crystals were dried under reduced pressure at 40° C. for 4 hours and further at room temperature for 12 hours to a crude crystals of N-[N-[3-(3-hydroxy-4-methoxyphenyl)propyl]-L-α-aspartyl]-L-phenylalanine 1-methyl ester (65.1 g, Content of the object compound: 54.4 g, Recovery rate: 82%). To the crude crystals (63.0 g) a mixed solvent (1740 ml) of methanol and water (Mixing ratio of 1:3 v/v) was added. The mixture was stirred for 30 minutes at 65° C. to dissolve the solid material, and thus obtained solution was cooled down to 10° C. (Cooling speed of 10° C./hour) to precipitate crystals. The mixture was stirred for 20 hours at the same temperature, and thus obtained crystals were separated by filtration and washed with a mixed solvent (250 ml) of methanol and water (Mixing ratio of 1:3 v/v), and dried under reduced pressure at 50° C. for 2.5 hours and further at room temperature for 12 hours to obtain N-[N-[3-(3-hydroxy-4-methoxyphenyl)propyl]-L-α-aspartyl]-L-phenylalanine 1-methyl ester (51.6 g, 113 mmol, Crystallization yield: 98%, Water content: 3.52 wt %). (The purity in HPLC was not less than 97%.)

For the crystals obtained above, diffractive X-ray was determined by using CuK α ray in the powder X-ray diffractometry. As a result, this crystal was in the crystalline form of A-type, which exhibits characteristic peaks of diffractive X-ray in at least diffraction angles of 8.2°, 14.7°, 20.5° and 22.4° (2 θ, CuK α ray) when determined in the powder X-ray diffractometry.

Example 3

Production of A-type Crystal of N-[N-[3-(3-hydroxy-4-methoxyphenyl)propyl]-L-α-aspartyl]-L-phenylalanine 1-methyl Ester and Separation of the Crystal (3)

To the crystals (10.0 g) obtained in Example 2, methanol (21 ml) was added and the crystals were dissolved at 40° C. Further, at the same temperature, water (13 ml) and isopropyl acetate (313 ml) were added thereto, and then the mixture was stirred. After a little, the crystals were precipitated. After that, the mixture was stirred for 5 hours at the same temperature and cooled down to 10° C. (Cooling speed of 10° C./hour) to precipitate crystals. The mixture was stirred for 15 hours at the same temperature, and thus obtained crystals were separated by filtration and dried under reduced pressure at 40° C. for 10 hours to obtain N-[N-[3-(3-hydroxy-4-methoxyphenyl)propyl]-L-α-aspartyl]-L-phenylalanine 1-methyl ester (9.78 g, Water content: 4.03 wt %). (The purity in HPLC was not less than 99%.)

For the crystals obtained above, diffractive X-ray was determined by using CuK α ray in the powder X-ray diffractometry. As a result, this crystal was in the crystalline form of A-type, which exhibits characteristic peaks of diffractive X-ray in at least diffraction angles of 8.2°, 14.7°, 20.5° and 22.4° (2 θ, CuK α ray) when determined in the powder X-ray diffractometry.

Example 4

Production of B-type Crystal of N-[N-[3-(3-hydroxy-4-methoxyphenyl)propyl]-L-α-aspartyl]-L-phenylalanine 1-methyl Ester and Separation of the Crystal (1)

3-(3-hydroxy-4-methoxyphenyl)propionaldehyde (1.40 g, 7.77 mmol) and aspartame (2.40 g, 8.15 mmol) were added to a mixed solvent (80 ml) of methanol and water (Mixing ratio of 4:1 v/v), and further 10% palladium on activated carbon in the water content of 50% (0.72 g) was added thereto. The reaction and the treatment of the mixture after the reaction were conducted in the same manner as those in Example 1 to obtain a reaction solution (81.2 g, 96 ml) containing N-[N-[3-(3-hydroxy-4-methoxyphenyl) propyl]-L-α-aspartyl]-L-phenylalanine 1-methyl ester (2.97 g, 6.48 mmol). This reaction solution was concentrated under reduced pressure at 50° C. to remove methanol by distillation. After that, water (360 ml) and ethyl acetate (90 ml) were added thereto and the solution thus obtained was stirred for 30 minutes at room temperature to prepare 2 layers separated therein. The ethyl acetate layer was removed to obtain an aqueous layer (444 g). This aqueous layer was concentrated under reduced pressure at 50° C. to remove the solvent by distillation. To this solution, methanol (4.5 ml) and ethyl acetate (90 ml) were added, and the solid material was dissolved therein at 65° C. The solution was cooled down to 10° C. (Cooling speed: 5° C./hour) to precipitate crystals. The mixture was stirred overnight at the same temperature, and then the crystals thus obtained were separated by filtration, and washed with ethyl acetate (90 ml). The crystals were dried overnight under reduced pressure at room temperature to obtain N-[N-[3-(3-hydroxy-4-methoxyphenyl)propyl]-L-α-aspartyl]-L-phenylalanine 1-methyl ester (2.75 g, 6.00 mmol, Crystallization yield: 93%, Water content: 0.435 wt %). (The purity in HPLC was not less than 92%.)

For the crystals obtained above, diffractive X-ray was determined by using CuK α ray in the powder X-ray diffractometry. As a result, this crystal was in the crystalline form of B-type, which exhibits characteristic peaks of diffractive X-ray in at least diffraction angles of 4.8°, 7.3°, 9.9° and 20.0° 2 θ, CuK α ray) when determined in the powder X-ray diffractometry.

Example 5

Production of B-type Crystal of N-[N-[3-(3-hydroxy-4-methoxyphenyl)propyl]-L-α-aspartyl]-L-phenylalanine 1-methyl ester and separation of the crystal (2)

To the crystals (10.0 g) obtained in Example 2, methanol (21 ml) was added, and the crystals were dissolved therein at 40° C. The mixture was cooled down to 10° C. Further, isopropyl acetate (313 ml) was added at the same temperature thereto, and the mixture was stirred. In a short time, the crystals were precipitated. After that, it was stirred at the same temperature for 23 hours. The crystals were separated by filtration and dried under reduced pressure at 40° C. for 10 hours to obtain N-[N-[3-(3-hydroxy-4-methoxyphenyl) propyl]-L-α-aspartyl]-L-phenylalanine 1-methyl ester (9.16 g, Water content of 0.431 wt %). (The purity in HPLC was not less than 99%.)

For the crystals obtained above, diffractive X-ray was determined by using CuK α ray in the powder X-ray diffractometry. As a result, this crystal was in the crystalline form of B-type, which exhibits characteristic peaks of diffractive X-ray in at least diffraction angles of 4.8°, 7.3°, 9.9° and 20.0° (2 θ, CuK α ray) when determined in the powder X-ray diffractometry.

Example 6

Production of C-type Crystal of N-[N-[3-(3-hydroxy-4-methoxyphenyl)propyl]-L-α-aspartyl]-L-phenylalanine 1-methyl Ester and Separation of the Crystal (1)

To the crystals (10.0 g) obtained in Example 2, methanol (21 ml) was added, and the crystals were dissolved therein at 40° C. Further, isopropyl acetate (313 ml) was added at the same temperature thereto for stirring. In a short time, the crystals were precipitated. After that, it was stirred at the same temperature for 5 hours, and then cooled down to 10° C. (Cooling speed of 10° C./hour) to precipitate the crystals. It was stirred at the same temperature for 15 hours and thus produced crystals were separated by filtration and dried under reduced pressure at 40° C. for 10 hours to obtain N-[N-[3-(3-hydroxy-4-methoxyphenyl)propyl]-L-α-aspartyl]-L-phenylalanine 1-methyl ester (9.41 g, Water content of 0.215 wt %). (The purity in HPLC was not less than 99%.).

For the crystals obtained above, diffractive X-ray was determined by using CuK α ray in the powder X-ray diffractometry. As a result, this crystal was in the crystalline form of C-type, which exhibits characteristic peaks of diffractive X-ray in at least diffraction angles of 4.7°, 8.0°, 9.0°, 14.0°, 20.2° and 24.3° (2 θ, CuK α ray) when determined in the powder X-ray diffractometry.

Example 7

Production of C-type Crystal of N-[N-[3-(3-hydroxy-4-methoxyphenyl)propyl]-L-α-aspartyl]-L-phenylalanine 1-methyl Ester and Separation of the Crystal (2)

To the crystals (10.0 g) obtained in Example 2, methanol (21 ml) was added, and the crystals were dissolved therein at 40° C. Further, water (0.75 ml) and isopropyl acetate (313 ml) were added thereto at the same temperature for stirring. In a short time, the crystals were precipitated. After that, it was stirred at the same temperature for 19 hours, and thus produced crystals were separated by filtration and dried under reduced pressure at 40° C. for 5 hours to obtain N-[N-[3-(3-hydroxy-4-methoxyphenyl)propyl]-L-α-aspartyl]-L-phenylalanine 1-methyl ester (9.40 g, Water content of 0.327 wt %). (The purity in HPLC was not less than 99%.)

For the crystals obtained above, diffractive X-ray was determined by using CuK α ray in the powder X-ray diffractometry. As a result, this crystal was in the crystalline form of C-type, which exhibits characteristic peaks of diffractive X-ray in at least diffraction angles of 4.7°, 8.0°, 9.0°, 14.0°, 20.2° and 24.3° (2 θ, CuK α ray) when determined in the powder X-ray diffractometry.

Example 8

Physical Properties on the A-type Crystal of N-[N-[3-(3-hydroxy-4-methoxyphenyl)propyl]-L-α-aspartyl]-L-phenylalanine 1-methyl Ester Physical properties on the title compound of the A-type crystal obtained in the present invention were in the followings.

Melting Point

99° C. (Determination in the differential thermal analysis; Temperature range for the determination: 50–300° C.; heating-up speed: 10° C./minute.)

<Powder X-Ray Diffraction>

Figure 1:
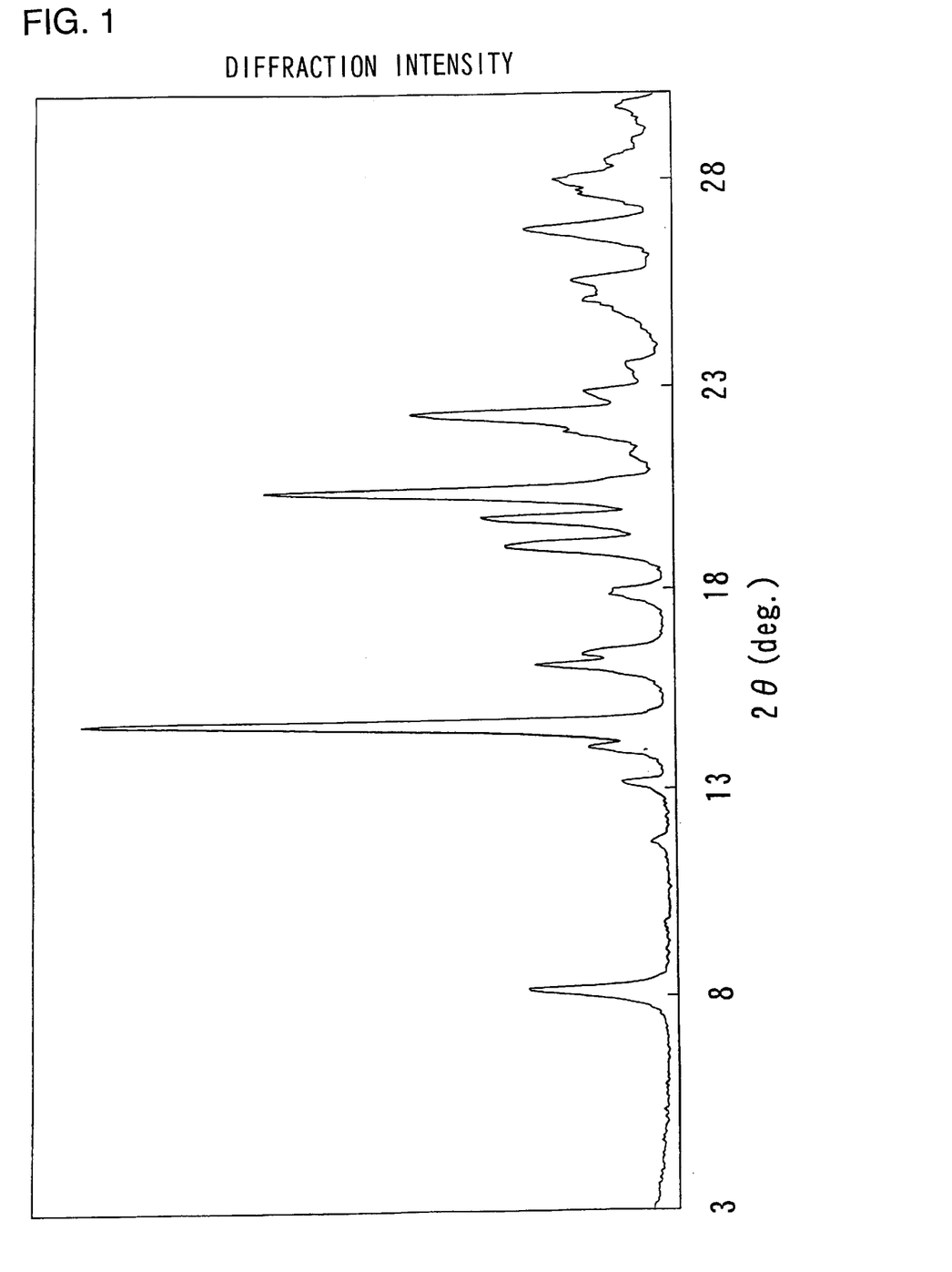
FIG. 1 is a powder X-ray diffraction pattern of A-type crystals of N-[N-[3-(3-hydroxy-4-methoxyphenyl)propyl]-L-α-aspartyl]-L-phenylalanine 1-methyl ester obtained according to the present invention.

The diffractive X-ray was determined in the powder X-ray diffractometry, and the obtained powder X-ray diffraction pattern was shown in the FIG. 1. As is evident from the FIG. 1, main X-ray diffractive peaks were observed in the diffraction angles of 8.2°, 14.7°, 16.1°, 19.1°, 19.8°, 20.5°, 22.4° and 26.9° (2 θ, CuK α ray).

The A-type crystal in the present invention can be characterized by the X-ray diffractive peaks of 8.2°, 14.7°, 20.5° and 22.4° (2 θ, CuK α ray) in the diffraction angles.

Example 9

Physical Properties on the B-type Crystal of N-[N-[3-(3-hydroxy-4-methoxyphenyl)propyl]-L-α-aspartyl]-L-phenylalanine 1-methyl Ester Physical properties on the title compound of the B-type crystal obtained in the present invention were in the followings.

<Melting Point>
123° C. (Determination in the differential thermal analysis; Temperature range for the determination: 50–300° C.; heating-up speed: 10° C./minute.)

Figure 2:
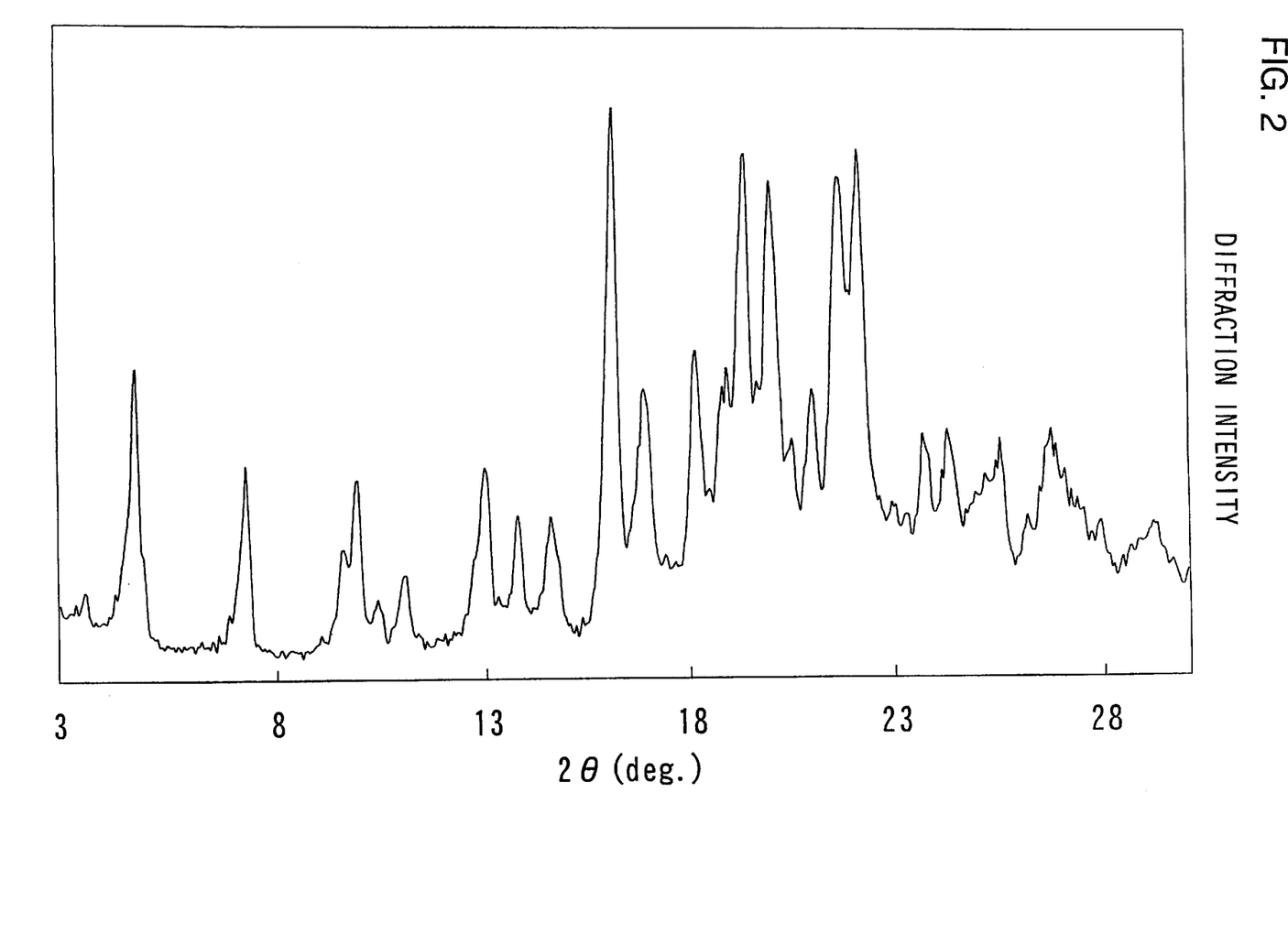
FIG. 2 is a powder X-ray diffraction pattern of B-type crystals of N-[N-[3-(3-hydroxy-4-methoxyphenyl)propyl]-L-α-aspartyl]-L-phenylalanine 1-methyl ester obtained according to the present invention.

<Powder X-Ray Diffraction>
The diffractive X-ray was determined in the powder X-ray diffractometry, and the obtained powder X-ray diffraction pattern was shown in the FIG. 2. As is evident from the figure, main X-ray diffractive peaks were observed in the diffraction angles of 4.8°, 7.3°, 9.9°, 13.0°, 16.2°, 16.9°, 18.2°, 19.5°, 20.0°, 21.7° and 22.2° (2 θ, CuK α ray).
The B-type crystal in the present invention can be characterized by the X-ray diffractive peaks of 4.8°, 7.3°, 9.9° and 20.0° (2 θ, CuK α ray) in the diffraction angles.

Example 10

Physical Properties on the C-type Crystal of N-[N-[3-(3-hydroxy-4-methoxyphenyl)propyl]-L-α-aspartyl]-L-phenylalanine 1-methyl Ester Physical properties on the title compound of the C-type crystal obtained in the present invention were in the followings.

<Melting Point>
138° C. (Determination in the differential thermal analysis; Temperature range for the determination: 50–300° C.; heating-up speed: 10° C./minute.)

Figure 3:
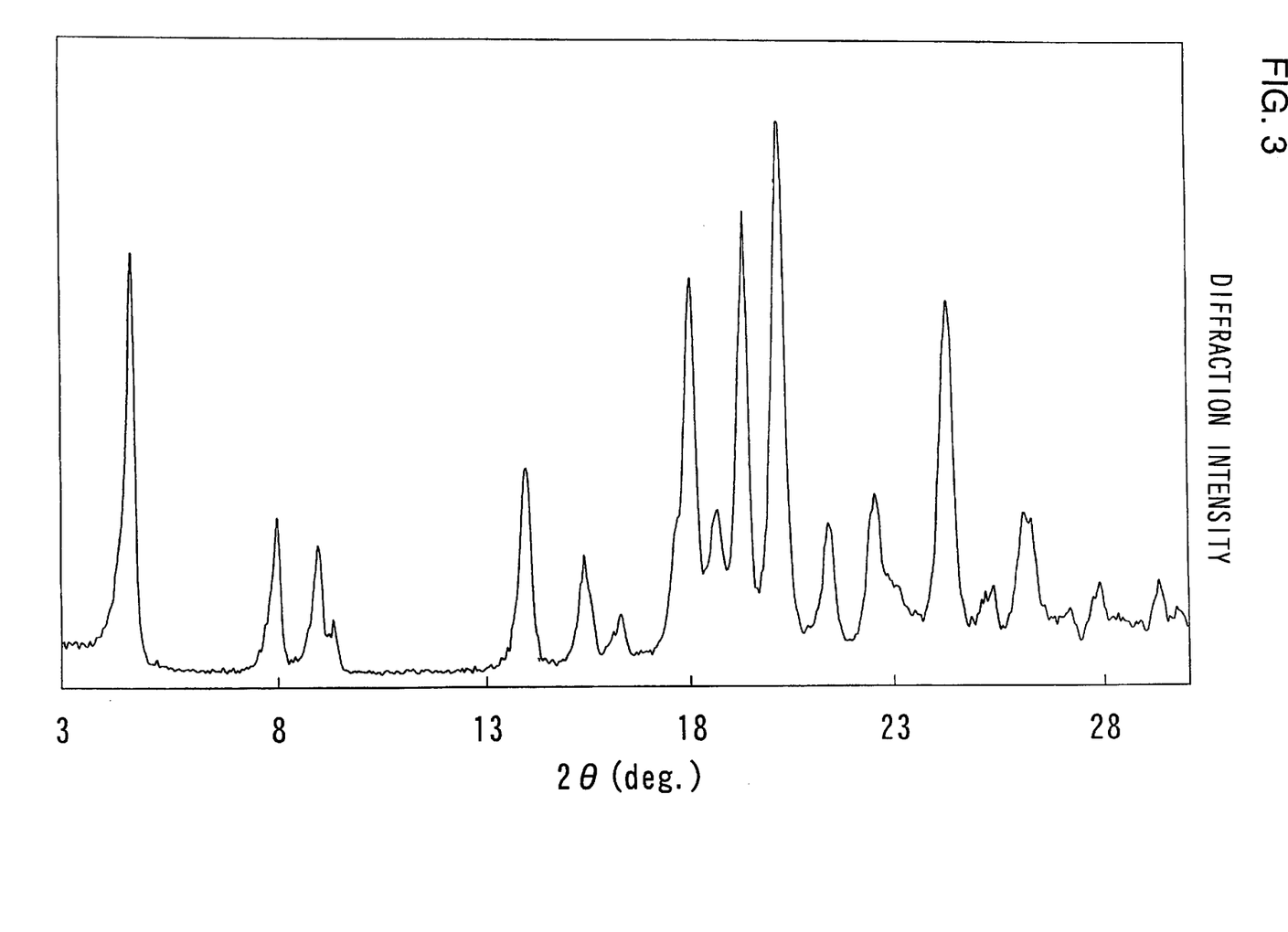
FIG. 3 is a powder X-ray diffraction pattern of C-type crystals of N-[N-[3-(3-hydroxy-4-methoxyphenyl)propyl]-L-α-aspartyl]-L-phenylalanine 1-methyl ester obtained according to the present invention.

<Powder X-Ray Diffraction>
The diffractive X-ray was determined in the powder X-ray diffractometry, and the obtained powder X-ray diffraction pattern was shown in the FIG. 3. As is evident from the figure, main X-ray diffractive peaks were observed in the diffraction angles of 4.7°, 8.0°, 9.0°, 14.0°, 18.1°, 18.7°, 19.4°, 20.2°, 21.4°, 22.6°, 24.3° and 26.1° (2 θ, CuK α ray).
The C-type crystal in the present invention can be characterized by the X-ray diffractive peaks of 4.7°, 8.0°, 9.0°, 14.0°, 20.2° and 24.3° (2 θ, CuK α ray) in the diffraction angles.

Example 11

Stabilities on N-[N-[3-(3-hydroxy-4-methoxyphenyl)propyl]-L-α-aspartyl]-L-phenylalanine 1-methyl Ester in Various Crystalline Forms and Amorphous Form An each sample (approximately 100 mg) of various type of crystals and amorphous form thereof was filled in the different two 10 ml-ampoules, respectively and the ampoules were sealed and kept at a temperature of 80° C. After 24 hours and 48 hours of reserve (storage) time, each one of the two ampoules containing the each sample was taken out and the sample was determined by the HPLC, whereby the residual ratio (survival rate) of N-[N-[3-(3-hydroxy-4-methoxyphenyl)propyl]-L-α-aspartyl]-L-phenylalanine 1-methyl ester was obtained. In such case, a relation between the reserve (storage) time and the residual ratio was shown in the following Table 1.

Results of stability test at 80° C.

| Samples | Reserve Time (hrs.) | | |
|---|---|---|---|
| | 0 | 24 | 48 |
| | Residual Ratio (%) | | |
| A-type crystal | 100 | 99 | 97 |
| B-type crystal | 100 | 98 | 97 |
| C-type crystal | 100 | 100 | 98 |
| Amorphous form | 100 | 65 | 44 |

In this manner, obviously any type of crystal was more stable than the amorphous form.

Obviously, numerous modifications and variations of the present invention are possible in light of the above teachings. It is therefore to be understood that within the scope of the appended claims, the invention may be practiced otherwise than as specifically described herein.

What is claimed is:

1. A crystal of N-[N-[3-(3-hydroxy-4-methoxyphenyl)propyl]-L-α-aspartyl]-L-phenylalanine 1-methyl ester, wherein said crystal is selected from the group consisting of:

(a) a crystal of N-[N-[3-(3-hydroxy-4-methoxyphenyl)propyl]-L-α-aspartyl]-L-phenylalanine 1-methyl ester, which exhibits at least X-ray diffraction peaks at diffraction angles of 8.2°, 14.7°, 20.5° and 22.4° (2 θ, CuK α ray) when examined by powder X-ray diffractometry;

(b) a crystal of N-[N-[3-(3-hydroxy-4-methoxyphenyl)propyl]-L-α-aspartyl]-L-phenylalanine 1-methyl ester, which exhibits at least X-ray diffraction peaks at diffraction angles of 4.8°, 7.3°, 9.9° and 20.0° (2 θ, CuK α ray) when examined by powder X-ray diffractometry; and (c) a crystal of N-[N-[3-(3-hydroxy-4-methoxyphenyl)propyl]-L-α-aspartyl]-L-phenylalanine 1-methyl ester, which exhibits at least X-ray diffraction peaks at diffraction angles of 4.7°, 8.0°, 9.0°, 14.0°, 20.2° and 24.3° (2 θ, CuK α ray) when examined by powder X-ray diffractometry.

2. A crystal of N-[N-[3-(3-hydroxy-4-methoxyphenyl)propyl]-L-α-aspartyl]-L-phenylalanine 1-methyl ester, which exhibits at least X-ray diffraction peaks at diffraction angles of 8.2°, 14.7°, 20.5° and 22.4° (2 θ, CuK α ray) when examined by powder X-ray diffractometry.

3. A crystal of N-[N-[3-(3-hydroxy-4-methoxyphenyl)propyl]-L-α-aspartyl]-L-phenylalanine 1-methyl ester, which exhibits at least X-ray diffraction peaks at diffraction angles of 4.8°, 7.3°, 9.9° and 20.0° (2 θ, CuK α ray) when examined by powder X-ray diffractometry.

4. A crystal of N-[N-[3-(3-hydroxy-4-methoxyphenyl)propyl]-L-α-aspartyl]-L-phenylalanine 1-methyl ester, which exhibits at least X-ray diffraction peaks at diffraction angles of 4.7°, 8.0°, 9.0°, 14.0°, 20.2° and 24.3° (2 θ, CuK α ray) when examined by powder X-ray diffractometry.

5. A method of making the crystal of claim 2, comprising crystallizing N-[N-[3-(3-hydroxy-4-methoxyphenyl)propyl]-L-α-aspartyl]-L-phenylalanine 1-methyl ester from a solvent comprising an organic solvent and water, wherein said organic solvent is selected from the group consisting of methanol, ethanol, isopropanol, acetone, tetrahydrofuran, and acetonitrile.

6. A method of making the crystal of claim 3, comprising crystallizing N-[N-[3-(3-hydroxy-4-methoxyphenyl)

propyl]-L-α-aspartyl]-L-phenylalanine 1-methyl ester from a solvent which is substantially free of water, wherein said solvent is a mixed solvent comprising a first solvent and a second solvent and wherein said first solvent is selected form the group consisting of methanol, ethanol, isopropanol, acetone, tetrahydrofuran, and acetonitrile and said second solvent is selected form the group consisting of methyl acetate, ethyl acetate, propyl acetate, isopropyl acetate, butyl acetate, diethyl ether, methyl t-butyl ether, and toluene.

7. A method of making the crystal of claim 4, comprising crystallizing N-[N-[3-(3-hydroxy-4-methoxyphenyl) propyl]-L-α-aspartyl]-L-phenylalanine 1-methyl ester from a solvent comprising an organic solvent and water, wherein said solvent is a mixed solvent comprising a first solvent and a second solvent and wherein said first solvent is selected from the group consisting of methanol, ethanol, isopropanol, acetone, tetrahydrofuran, and acetonitrile and said second solvent is selected from the group consisting of methyl acetate, ethyl acetate, propyl acetate, isopropyl acetate, butyl acetate, diethyl ether, methyl t-butyl ether, and toluene.

8. A method of sweetening a food or beverage product, comprising incorporating the crystal of claim 1 into a food or a beverage product.

9. A method of sweetening a food or beverage product, comprising incorporating the crystal of claim 2 into a food or a beverage product.

10. A method of sweetening a food or beverage product, comprising incorporating the crystal of claim 3 into a food or a beverage product.

11. A method of sweetening a food or beverage product, comprising incorporating the crystal of claim 4 into a food or a beverage product.

* * * * *

UNITED STATES PATENT AND TRADEMARK OFFICE
CERTIFICATE OF CORRECTION

PATENT NO. : 6,818,243 B2
DATED : November 16, 2004
INVENTOR(S) : Kazutaka Nagashima et al.

It is certified that error appears in the above-identified patent and that said Letters Patent is hereby corrected as shown below:

<u>Title page,</u>
Item [75], Inventors, "Kanagawa-ken" should read as -- Kawasaki-shi -- (all occurrances).

<u>Column 4,</u>
Line 61, "inbibits" should read as -- inhibits --.

<u>Column 10,</u>
Line 67, "stiffed" should read as -- stirred --.

<u>Column 17,</u>
Line 5, "form" should read as -- from --.
Line 14, "said solvent" should read as -- said organic solvent --.

Signed and Sealed this

Third Day of May, 2005

JON W. DUDAS
*Director of the United States Patent and Trademark Office*